US00PP29141P3

(12) United States Plant Patent
Wilson et al.

(10) Patent No.: US PP29,141 P3
(45) Date of Patent: Mar. 20, 2018

(54) ***CORDYLINE* PLANT NAMED 'LILLY'**

(50) Latin Name: *Cordyline australis*
Varietal Denomination: Lilly

(71) Applicants: Talbot Wilson, McGraths Hill (AU); Melinda Wilson, McGraths Hill (AU)

(72) Inventors: Talbot Wilson, McGraths Hill (AU); Melinda Wilson, McGraths Hill (AU)

( * ) Notice: Subject to any disclaimer, the term of this patent is extended or adjusted under 35 U.S.C. 154(b) by 8 days.

(21) Appl. No.: 14/998,545

(22) Filed: Jan. 16, 2016

(65) Prior Publication Data

US 2017/0208727 P1 Jul. 20, 2017

(51) Int. Cl.
*A01H 5/12* (2006.01)

(52) U.S. Cl.
USPC ..... Plt./383

(58) Field of Classification Search
USPC ..... Plt./383
See application file for complete search history.

(56) References Cited

PUBLICATIONS

Colourwise Summer Newsletter 2014-2015.*

* cited by examiner

*Primary Examiner* — Keith O Robinson
(74) *Attorney, Agent, or Firm* — C. A. Whealy

(57) ABSTRACT

A new and distinct cultivar of *Cordyline* plant named 'Lilly', characterized by its upright to semi-upright plant habit with leaves initially erect to outwardly arching; moderately vigorous growth habit; long lanceolate variegated leaves with brown and yellowish white-colored longitudinal stripes; and excellent keeping quality and good garden performance.

2 Drawing Sheets

Botanical designation: *Cordyline australis.*
Cultivar denomination: 'LILLY'.

BACKGROUND OF THE INVENTION

The present invention relates to a new and distinct *Cordyline* plant, botanically known as *Cordyline australis* and hereinafter referred to by the name 'Lilly'.

The new *Cordyline* plant is a naturally-occurring whole plant mutation of *Cordyline australis* 'Choc Mint', not patented. The new *Cordyline* plant was discovered and selected by the Inventors from within a population of plants of 'Choc Mint' in a controlled greenhouse environment in McGraths Hill, New South Wales, Australia during the spring of 2009.

Asexual reproduction of the new *Cordyline* plant by micropropagated cuttings in Tumbi Umbi, New South Wales, Australia since January, 2010 has shown that the unique features of this new *Cordyline* plant are stable and reproduced true to type in successive generations.

SUMMARY OF THE INVENTION

Plants of the new *Cordyline* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Lilly'. These characteristics in combination distinguish 'Lilly' as a new and distinct *Cordyline* plant:

1. Upright to semi-upright plant habit with leaves initially erect to outwardly arching.
2. Moderately vigorous growth habit.
3. Long lanceolate variegated leaves with brown and yellowish white-colored longitudinal stripes.
4. Excellent keeping quality and good garden performance.

Plants of the new *Cordyline* differ primarily from plants of the parent, 'Choc Mint', in leaf color as plants of 'Choc Mint' have greyed purple and green-colored leaves. In addition, plants of the new *Cordyline* have narrower leaves than plants of 'Choc Mint'.

Plants of the new *Cordyline* can be compared to plants of the *Cordyline australis* 'Torbay Dazzler', not patented. In side-by-side comparisons, plants of the new *Cordyline* differ primarily from plants of 'Torbay Dazzler' in leaf color as plants of 'Torbay Dazzler' have green and yellow variegated leaves.

BRIEF DESCRIPTION OF THE PHOTOGRAPHS

The accompanying photographs illustrate the overall appearance of the new *Cordyline* plant showing the colors as true as it is reasonably possible to obtain in colored reproductions of this type. Colors in the photographs may differ slightly from the color values cited in the detailed botanical description which accurately describe the colors of the new *Cordyline* plant.

The photograph on the first sheet comprises side perspective view of a typical plant of 'Lilly' grown in a container.

The photograph on the second sheet is a close-up view of a typical plant of 'Lilly'.

DETAILED BOTANICAL DESCRIPTION

The aforementioned photographs and following observations and measurements describe plants grown in August in 20-cm containers in a polyethylene-covered greenhouse in Keysborough, Victoria, Australia and under cultural practices typical of commercial *Cordyline* plant production. During the production of the plants, day temperatures averaged 18° C. and night temperatures averaged 8° C. Plants were 18 months old when the photographs and botanical description were taken. In the following description, color references are made to The Royal Horticultural Society Colour Chart, 2007 Edition, except where general terms of ordinary dictionary significance are used.

Botanical classification: *Cordyline australis* 'Lilly'.

Parentage: Naturally-occurring whole plant mutation of *Cordyline australis* 'Choc Mint', not patented.

Propagation:

*Type*.—By micropropagated cuttings.

*Time to initiate roots, summer*.—About 15 days at temperatures ranging from 20° C. to 25° C.

*Time to initiate roots, winter*.—About 20 days at temperatures ranging from 20° C. to 25° C.

*Time to produce a rooted young plant, summer*.—About 50 to 60 days at temperatures ranging from 20° C. to 25° C.

*Time to produce a rooted young plant, winter*.—About 70 to 80 days at temperatures ranging from 15° C. to 20° C.

*Root description*.—Medium in thickness, fleshy; typically white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Upright to semi-upright plant habit with leaves initially erect to outwardly arching; moderately vigorous growth habit; moderate growth rate.

*Plant height*.—About 60 cm.

*Plant diameter or spread*.—About 60 cm to 80 cm.

Leaf description:

*Arrangement*.—Whorled; sessile.

*Length*.—About 60 cm.

*Width*.—About 3 cm to 3.5 cm.

*Shape*.—Lanceolate or ensiform.

*Apex*.—Acute.

*Margin*.—Entire.

*Cross-sectional profile, full sunlight-grown plants*.—Towards the base, strongly concave, flattening towards the middle of the leaf to the apex.

*Texture, upper and lower surfaces*.—Leathery; ribbed; glabrous.

*Luster, upper and lower surfaces*.—Dull.

*Venation pattern*.—Parallel.

*Color*.—Developing leaves, upper surface: Longitudinal stripes, close to 200A and 144A to 144B. Developing leaves, lower surface: Longitudinal stripes, close to 200B and 144C. Fully expanded leaves, upper surface: Longitudinal stripes, close to 200A and 158A. Fully expanded leaves, lower surface: Longitudinal stripes, close to 200A and 158A. Venation, upper and lower surfaces: Similar to surface coloration.

Flower description: Flower initiation and development has not been observed on plants of the new *Cordyline*.

Disease & pest resistance: Plants of the new *Cordyline* have not been shown to be resistant to pathogens and pests common to *Cordyline* plants.

Keeping quality: Excellent keeping quality; plants of the new *Cordyline* are durable and will maintain good leaf substance indefinitely.

Garden performance: Plants of the new *Cordyline* have been observed to have good garden performance and to tolerate wind, rain and temperatures ranging from about 1° C. to about 47° C.

It is claimed:

1. A new and distinct *Cordyline* plant named 'Lilly' as illustrated and described.

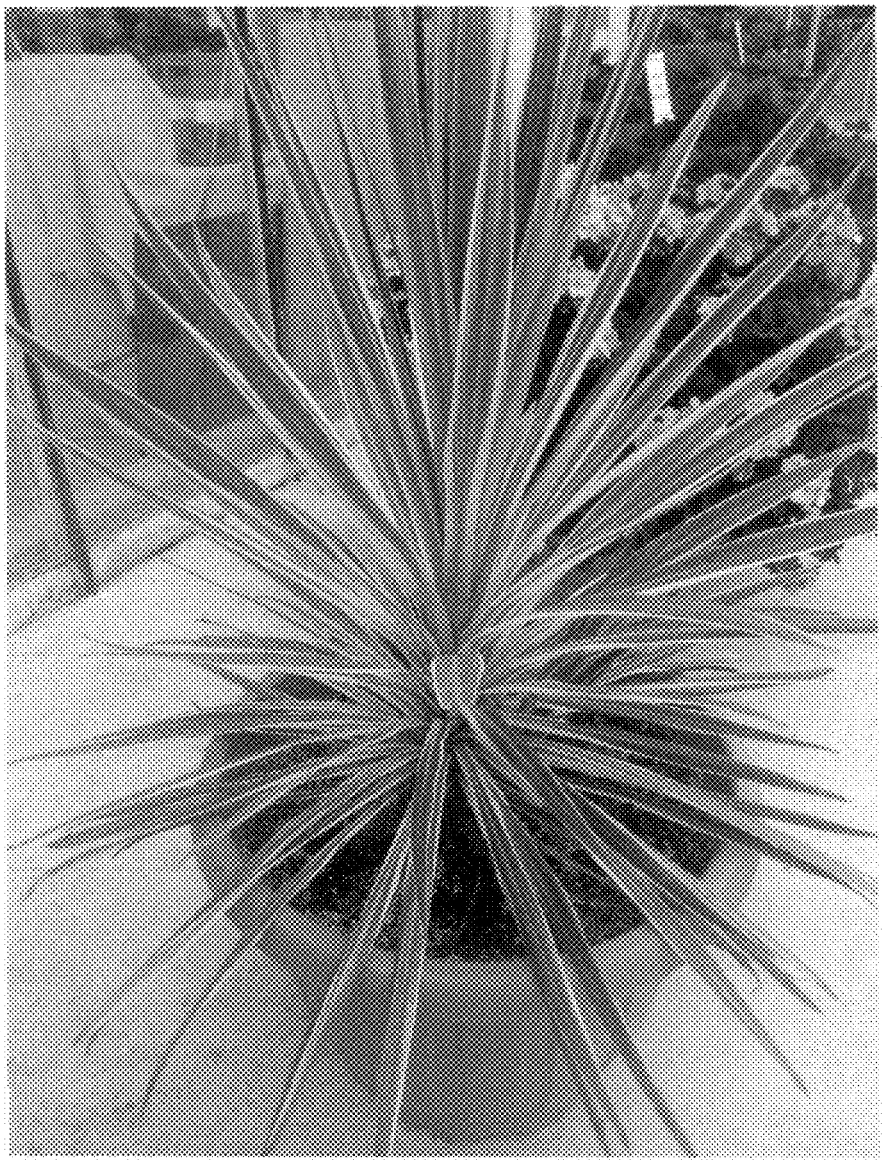

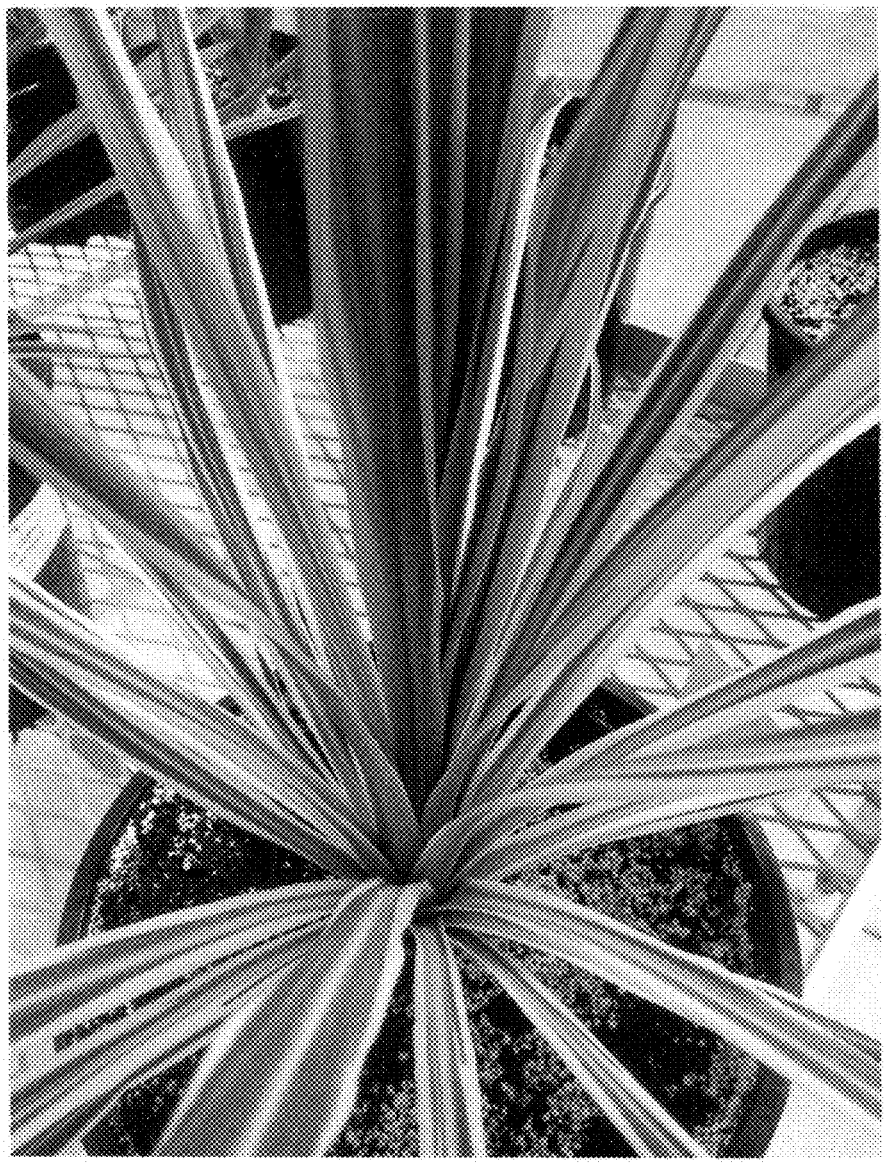

* * * * *